(12) United States Patent
Deniau et al.

(10) Patent No.: US 9,855,373 B2
(45) Date of Patent: Jan. 2, 2018

(54) IMPLANTABLE MATERIAL GRAFTED WITH A CELL ANTIPROLIFERATIVE AND/OR ANTIBACTERIAL FILM SYNTHETIZED FROM A BIFUNCTIONAL MOLECULE

(71) Applicants: BIOWINTECH, Paris (FR); COMMISSARIAT A L'ENERGIE ATOMIQUE ET AUX ENERGIES ALTERNATIVES (CEA), Paris (FR)

(72) Inventors: Guy Deniau, Les Essarts-le-Roi (FR); Cedric Zobrist, Bures-sur-Yvette (FR); Maxime Oudin, Paris (FR); Laurent David, Paris (FR)

(73) Assignees: BIOWINTECH, Paris (FR); COMMISSARIAT A L'ENERGIE ATOMIQUE ET AUX ENERGIES ALTERNATIVES (CEA), Paris (FR)

( * ) Notice: Subject to any disclaimer, the term of this patent is extended or adjusted under 35 U.S.C. 154(b) by 38 days.

(21) Appl. No.: 14/898,331

(22) PCT Filed: Jun. 13, 2014

(86) PCT No.: PCT/EP2014/062392
§ 371 (c)(1),
(2) Date: Dec. 14, 2015

(87) PCT Pub. No.: WO2014/198902
PCT Pub. Date: Dec. 18, 2014

(65) Prior Publication Data
US 2016/0129166 A1    May 12, 2016

(30) Foreign Application Priority Data
Jun. 14, 2013 (EP) .................................... 13172180

(51) Int. Cl.
| | | |
|---|---|---|
| *A61L 31/08* | (2006.01) | |
| *A61L 31/16* | (2006.01) | |
| *A61L 27/00* | (2006.01) | |
| *C07C 309/22* | (2006.01) | |
| *C07C 309/24* | (2006.01) | |
| *A61L 27/34* | (2006.01) | |
| *A61L 27/50* | (2006.01) | |
| *C07C 309/17* | (2006.01) | |
| *C07C 309/18* | (2006.01) | |

(52) U.S. Cl.
CPC ............... *A61L 31/16* (2013.01); *A61L 27/34* (2013.01); *A61L 27/50* (2013.01); *A61L 31/08* (2013.01); *C07C 309/17* (2013.01); *C07C 309/18* (2013.01); *C07C 309/22* (2013.01); *C07C 309/24* (2013.01); *A61L 2300/21* (2013.01); *A61L 2300/606* (2013.01); *A61L 2420/02* (2013.01); *A61L 2430/16* (2013.01)

(58) Field of Classification Search
None
See application file for complete search history.

(56) References Cited

U.S. PATENT DOCUMENTS

| | | |
|---|---|---|
| 4,490,529 A | 12/1984 | Rosowsky |
| 5,278,200 A | 1/1994 | Coury et al. |
| 6,218,492 B1 | 4/2001 | Hill et al. |
| 6,248,811 B1 | 6/2001 | Ottersbach et al. |
| 6,497,724 B1 | 12/2002 | Stevens et al. |
| 7,364,648 B2 | 4/2008 | Pinson et al. |
| 7,736,484 B2 | 6/2010 | Bureau et al. |
| 2006/0110430 A1 | 5/2006 | Pearson et al. |
| 2008/0145706 A1 | 6/2008 | Mevellec et al. |
| 2014/0088279 A1 | 3/2014 | Wolter et al. |

FOREIGN PATENT DOCUMENTS

| | | |
|---|---|---|
| CN | 1392139 A | 1/2003 |
| CN | 103130701 A | 6/2013 |
| EP | 2121814 A2 | 11/2009 |
| FR | 2910011 A1 | 6/2008 |

(Continued)

OTHER PUBLICATIONS

Yammine et al. "Surface Modification of Silicone Intraocular Implants to Inhibit Cell Proliferation." Biomacromolecules, vol. 6, No. 5, Aug. 2005, pp. 2630-2637.

(Continued)

*Primary Examiner* — Kevin S Orwig
(74) *Attorney, Agent, or Firm* — Young & Thompson

(57) ABSTRACT

The present invention relates to an implantable material having at least one external surface grafted with a film including carboxylate and sulfonate functions wherein the film is simultaneously synthesized and grafted directly on the external surface by radical reaction of a bifunctional adhesion primer of Formula (I) or by radical reaction of an adhesion primer and a bifunctional polymerizable monomer of Formula (II).

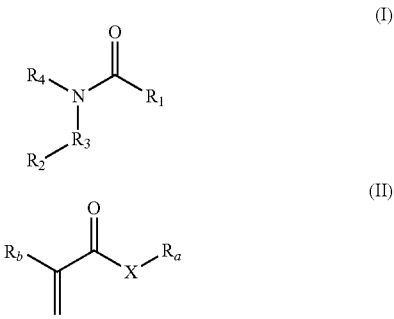

The invention also relates to a process for directly synthesizing and grafting of a film according to the invention onto at least one external surface of an implantable material. The invention further relates to the use of a grafted implantable material for the manufacture of an antiproliferative and/or antibacterial implantable medical device. The invention also relates to compounds of Formula (I) and Formula (II).

10 Claims, 2 Drawing Sheets

(56) References Cited

FOREIGN PATENT DOCUMENTS

| JP | S6372332 | A  | 4/1988  |
|----|----------|----|---------|
| JP | 5179155  | A  | 7/1993  |
| JP | 2000198782 | A | 7/2000 |
| WO | 03018212 | A1 | 3/2003  |
| WO | 2008078052 | A2 | 7/2008 |
| WO | 2008090554 | A2 | 7/2008 |
| WO | 2012163781 | A1 | 12/2012 |
| WO | 2013186388 | A1 | 12/2013 |

OTHER PUBLICATIONS

Lyskawa et al. "Direct Modification of a Gold Electrode with Aminophenyl Groups by Electrochemical Reduction of in Situ Generated Aminophenyl Monodiazonium Cations." Chemistry of Materials, vol. 18, No. 20, Sep. 2006, pp. 4755-4763.

Uzulina et al. "Synthesis of polymer colloids using polymerizable surfactants." Macromolecular Chemistry and Physics, Wiley-VCH , Verlag, Weinheim, vol. 202, No. 16, Nov. 2001, pp. 3126-3135.

Rosowsky et al. "Methotrexate analogs, 19. Replacement of the glutamate side chain in classical antifolates by L-homocysteic acid and L-cysteic acid: effect on enzyme inhibition and antitumor activity." Journal of Medicinal chemistry, vol. 27, No. 5, May 1984, pp. 600-604.

European Search Report, dated Feb. 21, 2014, from European Application No. EP13172180.

International Search Report, dated Sep. 4, 2014, from International Application No. PCT/EP2014/062392.

European Search Report, dated Nov. 21, 2012, from European Application No. EP12172281.

International Search Report, dated Jul. 30, 2013, from International Application No. PCT/EP2013/062444.

IMPLANTABLE MATERIAL GRAFTED WITH A CELL ANTIPROLIFERATIVE AND/OR ANTIBACTERIAL FILM SYNTHETIZED FROM A BIFUNCTIONAL MOLECULE

FIELD OF INVENTION

The present invention relates to an implantable material whose surface is grafted with a cell antiproliferative film. Especially, the present invention relates to an intraocular lens (IOL) whose surface is grafted with a cell antiproliferative film. The cell antiproliferative film of the invention comprises free carboxylate and sulfonate functions in a 1:1 molar ratio, said functions being introduced in the film by the use in its synthesis of bifunctional adhesion primer of Formula (I) or bifunctional polymerizable monomers of Formula (II). The present invention also relates to a process for grafting a cell antiproliferative a film at the surface of an implantable material, preferably an IOL. The invention further relates to bifunctional compounds of Formula (I) and (II) bearing one carboxylate function and one sulfonate function:

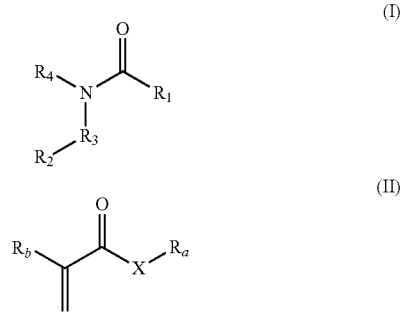

wherein $R_1$, $R_2$, $R_3$, $R_4$, X, $R_a$ and $R_b$ are as described below.

BACKGROUND OF INVENTION

Most of materials that are implanted in the organism or simply transiting inside thereof need to be at least biocompatible. Implantable materials often need to further have antirejection, cell antiproliferation and antibacterial properties.

For example, in order to avoid restenosis after stent implantation in an artery, the stent may have antirejection and/or antiproliferation properties. Chemists have developed a coating that may be physisorbed on the stent, said coating comprising an antirejection drug that is sustainingly released in blood.

Another example pertains to the field of ocular implants for which cell antiproliferation properties may be needed. Indeed, in order to avoid cataract, the sole efficient treatment consists in a surgical operation during which the crystalline lens is replaced by an intraocular implant (IOL). The most frequent post-operative complication of this treatment is the development of a cicatricial tissue around the implant, leading to an opacification and that is called secondary cataract. A second surgical operation is thus needed to solve this opacification problem. This side effect appears in 38% of patients about 9 years after the implantation of the IOL. Solutions are therefore expected to avoid secondary cataract and are searched through three main axes:
- improvement of surgical methods: more precise methods are tested, especially in order to reduce the size of the incision and therefore avoid ocular traumatisms;
- study of the implant geometry: it has been shown that certain forms of lens provide a mechanical barrier that avoid cell migration between the implant and the eye capsule;
- use of new materials and/or surface treatments in order to improve biocompatibility and/or to bring new functionalities.

Intraocular lens are mainly obtained from 3 types of materials: silicones, hydrophobic methacrylates and hydrophilic methacrylates. These materials are biocompatible and have convenient physical and optical properties. However, these materials do not have particular cell antiproliferation properties. Therefore, the development of new material or surface treatment bringing cell antiproliferation properties to IOL is needed. Further antibacterial properties are also of interest.

More generally, it is a general concern that implantable materials shall have cell antiproliferation properties in order to avoid colonization when implanted and further antibacterial properties are valuable to avoid the development of infections.

It was described in the prior art that certain chemical functions, when present at the surface of materials, may give cell antiproliferation and/or antibacterial properties to said material. Especially, mimicking heparin by using the association of carboxylate and sulfonate functions, in specific ratios, may confer cell antiproliferation and/or antibacterial properties to the substrate on which it is present.

Coatings comprising carboxylate and sulfonate functions of substrates for use in medical applications are for example described in U.S. Pat. No. 6,248,811. These coating are films which are first synthesized and isolated, then coated on the surface and finally grafted under UV radiative induction on the surface. Depending on the molar ratio of carboxylate functions to sulfonate functions, the coating polymers of U.S. Pat. No. 6,248,811 have:
- antibacterial properties, for a molar ratio of carboxylate functions to sulfonate functions ranging preferably from 0.1 to 5;
- antibacterial properties together with cell proliferation-inhibiting properties, for a molar ratio carboxylate/sulfonate ranging preferably from 0.4 to 2; or
- cell proliferation-promoting properties, for a molar ratio carboxylate/sulfonate ranging preferably from 3 to 5.

In this document, it is described that, depending on the value of the molar ratio of carboxylate functions to sulfonate functions, the coating polymers may have antibacterial properties and can be formulated so as to inhibit or promote cell proliferation. However, U.S. Pat. No. 6,248,811 discloses a method comprising several steps, i.e. the separate synthesis of the polymer, the isolation of the polymer, the coating of the polymer onto the substrate and then the graft of the polymer onto the coating by UV radiative induction. This technique is hardly industrially operable.

It is reported in the literature that a molar ratio of carboxylate functions to sulfonate functions equal to 1 could be optimum to inhibit cell proliferation, while displaying antibacterial properties. However, providing a thin grafted film (less than 100 nm), with a balanced 1:1 proportion of carboxylate functions and sulfonate functions is not made possible by the prior art techniques. Also, controlling the grafting of the material, and the presence of the ratio, may be a technical or quality-control issue, especially with thin coatings.

The present invention intends providing an implantable material presenting at its surface carboxylate and sulfonate functions in a 1:1 molar ratio, this ratio being securely and easily assessable and controlled.

Moreover, it is important that the coating comprising the carboxylate and sulfonate functions be chemically grafted on the implantable material, and not simply adsorbed thereon, in order to ensure a greater functional longevity to the material. Therefore, one object of the invention is to provide an implantable material chemically grafted on its surface with carboxylate and sulfonate functions in a 1:1 molar ratio.

In a preferred embodiment, implantable materials are organic implantable material, especially IOLs.

The process of manufacturing of the material chemically grafted carboxylate and sulfonate functions in a 1:1 molar ratio should be simple, reproducible and industrializable.

Known materials grafted with coatings comprising carboxylate and sulfonate functions are mainly obtained by first synthesizing and isolating a polymer comprising the carboxylate and sulfonate functions, the coating the polymer on the material and finally grafting it by chemical reaction, such as for example by UV curing as in U.S. Pat. No. 6,248,811.

U.S. Pat. No. 6,218,492 discloses a water-insoluble polymer, with antibacterial and/or antiproliferative properties. This polymer is synthesized by free-radical copolymerization of component I (containing a carboxyl group), component II (containing a sulfonic acid group), and component III (which is an aliphatically unsaturated monomer). The polymer may either be used as implantable constitutive material or being coated at the surface of an implant. However, this polymer presents low mechanical properties that render it difficult to be processed as constitutive material and affect its resistance overtime when coated as a layer.

Yammine et al. also described coatings comprising carboxylate and sulfonate functions (Yammine et al., Biomacromolecules, 2005, 6(5), 2630-2637). Especially, they developed photo-crosslinkable polymers bearing cinnamic, sulfonate and carboxylate functions to coat silicon intraocular lenses in order to reduce "secondary cataract" by inhibiting cell proliferation. The polymer is first synthesized by radical polymerization and then grafted on the IOL after coating by cycloaddition reaction of photosensible groups.

Methods presented above present the inconvenient to be at least two-steps methods, requiring first the synthesis of the polymer and then its grafting on the surface of the material. With these methods, the molar ratio of carboxylate function to sulfonate function cannot be precisely controlled in a simple and reproducible manner to obtain exactly a 1:1 molar ratio.

Coury et al. described, in in patent U.S. Pat. No. 5,278,200, heparin-like material and surfaces made by co-polymerization of acrylic acid (AA) and 2-acrylamido-2-methyl propane sulfonic acid (AMPS) in order to decrease bacterial and platelet adherence. The polymer may be first synthesized and then grafted on the material. The polymer may also be directly synthesized and grafted on the material by the generation of free radicals on the material surface (such as polyurethane surface), using Ce(IV) ions and radical copolymerization of AA and AMPS. However, grafting using Ce(IV) ions at the surface of the material presents, among others, the following drawbacks:

the method is not versatile as it may only be performed on materials comprising oxidizable functions at their surfaces;

cerium ions remain at the surface of the grafted material, which is incompatible with biological applications as cerium ions are toxic;

the polymerization should be performed under controlled atmosphere, need an energy intake as it has to be performed at 40° C. and is slow, usually at least 3 hours, in other words this method is not easily industrializable.

Moreover, the control of the carboxylate to sulfonate functions cannot be precisely controlled in a simple and reproducible manner to obtain exactly a 1:1 molar ratio.

The Applicant previously developed a simple and efficient process to chemically graft carboxylate and sulfonate functions on implantable materials, especially on organic implantable materials such as IOLs. The method is described in patent application EP 12 172 281.3.

The process developed by the Applicant is based on a method which makes it possible to perform the grafting of organic polymer or copolymer films on the implantable material in the absence of an electric voltage (EP 2 121 814). This method, used under the name Graftfast®, makes it possible to graft films onto surfaces of various types, even non-conductive surfaces.

The Graftfast® method enables chemically grafting an organic film at the surface of a solid support. The method is based on chemical reactions, essentially radical reactions of chemisorption and polymerization, hereafter referred to as "copolymerization-like reaction".

In classical radical polymerization or copolymerization, a first monomer is added on a radical initiator to form a radical building block, which constitutes the basis on which the polymer will grow. Further non-radical monomers, identical or different, are then successively added on the growing free radical copolymer as represented on FIG. 1-A.

Contrary to classical radical polymerization, in the copolymerization-like reaction of Graftfast®, the growing polymer does not bear a radical. It requires at each step the use of an activator to generate a radical entity which is then added on the growing polymer (FIG. 1-B).

The Graftfast® method may be implemented using adhesion primers as sole building entities. Adhesions primers are molecules capable of being chemisorbed at the surface of the substrate by radical reaction and comprising a further reactive function capable radical polymerization with another radical after chemisorption. Generally, the adhesion primer includes diazonium salts which strong reactivity ensures a robust covalent link between the polymer film and the substrate. The reaction of the diazonium salts with a chemical activator having reducing properties allows the reduction of the diazonium and generation of radicals. The activator may be a chemical agent but it may also be a physical condition, such as for example a given temperature or a photoactivation.

The adhesion primer, activated under the form of a radical, first reacts with the surface, forming a primary layer of adhesion. Simultaneously, further adhesion primers activated under the form of radicals react with this grafted primary layer of adhesion, to synthesize the film by radical polymerization directly on the surface.

The Graftfast® method may also be implemented using adhesion primers in combination with polymerizable monomers. The first steps of chemisorption of the adhesion primer on the surface and of its polymerization on the surface are the same as described above. At the same time, adhesion primers activated under the form of radicals react with the polymerizable monomers to form radical building blocks. This initiates the polymerization of the polymerizable monomer. Growing polymeric chains then react with the growing film anchored on the surface. A copolymer is thus directly synthesized on the surface by radical copolymerization after radical chemisorption of the adhesion primer.

Therefore, the Graftfast® method is implemented on a substrate using an adhesion primer, in a solvent, in presence of an activator and optionally in presence of polymerizable monomers. The film is simultaneously grafted and synthesized directly at the surface of the substrate.

The Graftfast® method had never been used to graft carboxylate and sulfonate functions in controlled ratio on implantable materials.

The Applicant performed an extensive research work to make it possible to carry out the Graftfast® technology for the specific goal of providing carboxylate and sulfonate grafted surfaces in a reproducible and controlled manner. It resulted in an implantable material grafted at the surface thereof with a film comprising carboxylate and sulfonate functions wherein the film is directly synthesized and grafted on said external surface by radical reaction of a source of carboxylate functions and a source of sulfonate functions, said sources being either polymerizable or chemisorbable and polymerizable.

Especially, this method was implemented using a chemisorbable and polymerizable adhesion primer having a carboxylate function in combination with a polymerizable monomer comprising a sulfonate function, leading to a film grafted on the surface.

In order to simply and reproductively obtain a molar ratio of carboxylate to sulfonate functions equal to 1, the Applicant sought to use bifunctional reactants, comprising one carboxylate function and one sulfonate function. By having the two functions on the same building block, the control of the ratio is automatically obtained.

However, the Applicant did not find any commercial compounds being susceptible to be used as adhesion primers in the Graftfast® technology. Therefore, the Applicant developed new functional adhesion primers having both one carboxylate function and one sulfonate function of Formula (I).

Moreover, the Applicant also developed bifunctional polymerizable monomers having both one carboxylate function and one sulfonate function of Formula (II), to be used together with any suitable adhesion primer in the Graftfast® technology.

Therefore, the invention relates to implantable materials grafted with a film simultaneously synthesized and grafted by contacting the surface of the material with a solution comprising the new bifunctional adhesion primer of Formula (I) or the bifunctional polymerizable monomer of Formula (II) of the invention, in conditions providing radicals.

DEFINITIONS

In the present invention, the following terms have the following meanings:

"about" preceding a figure means plus or less 10% of the value of said figure.

"implantable material" refers in the meaning of the present invention to a material and/or a medical device that is at least biocompatible and may be introduced and left within a living body without triggering immune reactions.

"implantable medical device" refers to a medical device that is at least biocompatible and may be introduced and left within a living body without triggering immune reactions and may be for example implants, intraocular lenses (IOLs), stents, catheters, implants for abdominal surgery, vascular prostheses, artificial limbs.

"implantation device" or "inserting device" refers to a device that is used to insert an implantable medical device within a living body. Especially, an intraocular lens may be implanted using IOL-inserting device.

"grafted surface" refers to a surface on which a coating is chemically anchored. In the present invention, a grafted surface should be understood in contrast with a coated surface, wherein the coating is just adsorbed onto the surface.

"organic film" or "film" refers to any polymer or copolymer film, resulting from the copolymerisation like reaction of a plurality of monomer units of identical or different chemical species and adhesion primer molecules. The films obtained by the method of the present invention are essentially incorporates species resulting from the adhesion primer and from polymerizable monomers.

"copolymerization-like reaction" refers to a method by which a polymer is formed by the successive addition of free radical building blocks. In the present invention, the copolymerization-like reaction is performed in presence of an adhesion primer and of an activator. In one embodiment, the copolymerization-like reaction is performed in presence of at least two different adhesion primers and of an activator. In another embodiment, the copolymerization-like reaction is performed in presence of at least one adhesion primer, at least one polymerizable monomer and an activator.

"chemisorbable" stands for capable, under certain conditions, of being chemically anchored at the surface of a implantable material.

"polymerizable" refers to a monomer for capable, under certain conditions, to be used for the synthesis of a polymer or an oligomer.

"adhesion primer" refers to an organic molecule capable, under certain conditions, of being chemisorbed at the surface of a solid implantable material by a radical chemical grafting, and comprising a reactive function with respect to another radical after chemisorption. An adhesion primer is thus chemisorbable and polymerizable. In a preferred embodiment of the invention, adhesion primers comprise a diazonium salts moiety enabling their chemisorption at the surface of a implantable material by radical reaction. According to an embodiment, a "bifunctional adhesion primer" in the present invention refers to an adhesion primer comprising one carboxylate function and one sulfonate function.

"polymerizable monomer" refers to an organic molecule comprising a functional moiety, capable, under certain conditions, to be used as a monomer for the synthesis of a polymer. In one embodiment of the present invention, the polymerizable monomer is a polymerizable vinylic monomer, which refers to an organic molecule comprising a vinyl moiety, capable, under certain conditions, to be used as a monomer for the synthesis of a polymer. According to an embodiment, a "bifunctional polymerizable monomer" in the present invention refers to a polymerizable monomer having both carboxylate and sulfonate moieties, preferably comprising one carboxylate function and one sulfonate function.

"activator" refers to a chemical compound, such as a compound with reducing properties, or a physical condition, such as temperature or photoactivation, that allows the initiation of copolymerization-like reaction.

"conditions enabling the formation of radical entities" comprise the use of an activator according to the present invention.

"protic solvent" refers to a solvent that comprises at least one hydrogen atom capable of being released in proton form.

"cell antiproliferative" or "that inhibit cell proliferation" refers to the property of at least limiting cell colonization, i.e. limiting adhesion and/or multiplication of cells, on the surface that has cell antiproliferative properties. In the present invention, a implantable material whose surface is grafted or coated with a cell antiproliferative film refers to the fact that said film has the property to limit cell colonization on said surface.

"antibacterial" refers to the property of limiting bacteria proliferation. In the present invention, a implantable material whose surface is grafted or coated an antibacterial film refers to the fact that said film has the property to limit bacteria proliferation on said surface.

"cytostatic" refers to the property to prevent cell growth.

"cytotoxic" refers to the property to induce cell death.

"source of carboxylate functions" refers to a chemical compound comprising at least one carboxylic acid function or at least one carboxylate salt function.

"source of sulfonate functions" refers to a chemical compound comprising at least one sulfonic acid function or at least one sulfonate salt function.

"carboxylate function", according to the present invention refers to carboxylic acid function or carboxylate salt function.

"carboxylic acid function" refers to the chemical formula —COOH.

"carboxylate salt function" refers to the formula —COO$^-$X$^+$ wherein X is an inorganic or organic cation, preferably sodium, potassium, magnesium, calcium.

"sulfonate function" according to the present invention refers to sulfonic acid function or sulfonate salt function.

"sulfonic acid function" refers to the chemical formula —SO$_3$H.

"sulfonate salt" refers to the formula —SO$_3^-$X$^+$ wherein X is an inorganic or organic cation preferably sodium, potassium, magnesium, calcium.

"alkyl" refers to any saturated linear or branched hydrocarbon chain, with 1 to 12 carbon atoms, preferably 1 to 6 carbon atoms, and more preferably methyl, ethyl, propyl, isopropyl, n-butyl, sec-butyl, isobutyl and tert-butyl.

"aryl" refers to a polyunsaturated, aromatic hydrocarbyl group having a single ring or multiple aromatic rings fused together (such as naphthyl) or linked covalently, typically containing 5 to 20, and preferably 6 to 12, carbon atoms having one or more aromatic rings among which it is possible to cite the phenyl group, the biphenyl group, the 1-naphthyl group, the 2-naphthyl group, the tetrahydronaphthyl group, the indanyl group and the binaphthyl group.

"heteroaryl" refers to 5 to 12 carbon-atom aromatic rings or ring systems containing 1 to 2 rings which are fused together or linked covalently, typically containing 5 to 6 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1 (2H)-yl, 6-oxo-pyrudazin-1(6H)-yl, 2-oxopyridin-1(2H)-yl, 1,3-benzodioxolyl, quinolinyl, isoquinolinyl, cinnolinyl, quinazolinyl, quinoxalinyl.

"halogen" refers to fluoro, chloro, bromo or iodo, Preferred halogen groups are fluoro and chloro.

"carbonyl" refers to the group —(C=O)—. Alkylcarbonyl refers to an alkyl-(C=O)— group, alkyl being as defined herein.

"primary amine group" refers to a —NH$_2$ group.

"diazonium salt group" refers to an organic compound comprising a —N$_2^+$Y$^-$ functional group wherein Y$^-$ is an inorganic or organic anion, preferably Cl$^-$ or BF$_4^-$.

"nitro" refers to a —NO$_2$ group.

In the present invention and unless otherwise stated, the normal conditions of temperature and pressure correspond to a temperature of 25° C. and to a pressure of 1.10$^5$ Pa.

DETAILED DESCRIPTION

Grafted Implantable Material

The present invention relates to an implantable material grafted with a film comprising carboxylate and sulfonate functions wherein the film is produced by a copolymerization-like reaction involving a molecule, hereinafter called bifunctional molecule, having both carboxylate functions and sulfonate functions.

In an embodiment, the implantable material of the invention has at least one external surface grafted with a film comprising carboxylate and sulfonate functions wherein the film is simultaneously synthesized and grafted directly on said external surface by radical reaction of:

a bifunctional adhesion primer of Formula (I)

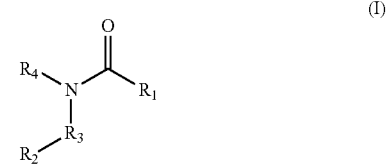

wherein

R1 represents a group substituted by one carboxylate function and one sulfonate function, said group being selected from linear or branched alkyl, aryl, heteroaryl; said groups being optionally substituted by one or more substituent selected from alkyl, aryl, halogen or carbonyl;

R2 represents an aryl or heteroaryl group substituted by at least one diazonium salt group and optionally further substituted by one or more substituent selected from alkyl, aryl or halogen;

R3 is absent or represents or a linear or branched C1-C3 alkyl group, optionally substituted by one or more substituent selected from alkyl, aryl, heteroaryl, halogen or nitro;

R4 represents a hydrogen atom or a group selected from alkyl, aryl, heteroaryl or carbonyl;

or an adhesion primer and a bifunctional polymerizable monomer of Formula (II)

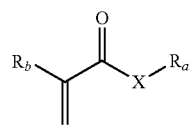
(II)

wherein $R_a$ represents a group substituted by one carboxylate function and one sulfonate function, said group being selected from linear or branched alkyl, acyloxyalkyl, alkylcarbonyloxyalkyl, arylcarbonyloxyalkyl, alkylcarbonyloxyaryl, alkyloxycarbonylalkyl, aryloxycarbonylalkyl, alkyloxycarbonylaryl, optionally comprising heteroatoms in the main chain; said groups being optionally substituted by one or more substituent selected from alkyl, aryl, halogen or carbonyl groups; preferably, $R_a$ is an arylcarbonyloxyalkyl or an alkylcarbonyloxyalkyl group substituted by one carboxylate function and one sulfonate function; more preferably, $R_a$ is benzenecarbonyloxyethyl or ethylcarbonyloxyethyl group substituted by one carboxylate function and one sulfonate function;

$R_b$ represents H or methyl;

X represents O or NH.

In one embodiment, the film is simultaneously synthesized and grafted directly on the external surface by radical chemisorption and polymerization of a bifunctional adhesion primer of Formula (I)

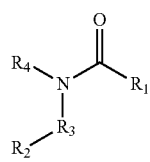
(I)

wherein

R1 represents a group substituted by one carboxylate function and one sulfonate function, said group being selected from a C1-C4 linear or branched alkyl, more preferably R1 represents a sulfopropanoic or a sulfobutanoic acid;

R2 represents an aryl or heteroaryl group substituted by at least one diazonium salt group and optionally further substituted by one or more substituent selected from alkyl, aryl or halogen; preferably a benzodiazonium;

R3 is absent or represents a linear or branched C1-C3 alkyl group, optionally substituted by one or more substituent selected from alkyl, aryl, heteroaryl, halogen or nitro; preferably R3 is absent;

R4 represents a hydrogen atom or a group selected from alkyl, aryl, heteroaryl or carbonyl; preferably hydrogen atom.

According to one embodiment, the diazonium salt function substituting R2 in compound of Formula (I) may be obtained by reacting the corresponding compound, substituted on R2 by a primary amine, with sodium nitrite.

In one embodiment, the primer of formula (I) as shown above is such that:

R1 represents a group substituted by one carboxylate function and one sulfonate function, said group being selected from a C2-C4, preferably C2-C3 alkyl;

R2 represents an benzodiazonium group;

R3 is absent;

R4 represents a hydrogen atom.

Two examples of preferred compounds of formula (I) are shown below:

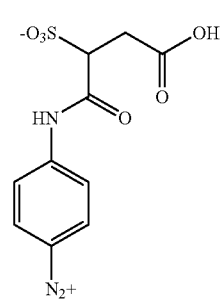
Ia

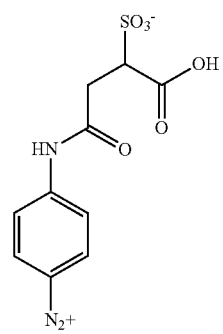
Ib

According to one embodiment, the diazonium salt function substituting R2 in compound of Formula (I) may be obtained by reacting the corresponding compound, substituted on R2 by a primary amine (preferably aniline), with sodium nitrite.

According to another embodiment, the film is simultaneously synthesized and grafted directly on the external surface by radical chemisorption an adhesion primer and its polymerization with a bifunctional polymerizable monomer of Formula (II)

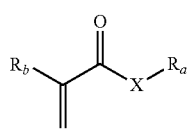

(II)

wherein
$R_a$ represents a group substituted by one carboxylate function and one sulfonate function, said group being selected from linear or branched alkyl, acyloxyalkyl, alkylcarbonyloxyalkyl, arylcarbonyloxyalkyl, alkylcarbonyloxyaryl, alkyloxycarbonylalkyl, aryloxycarbonylalkyl, alkyloxycarbonylaryl; optionally comprising heteroatoms in the main chain; said groups being optionally substituted by one or more substituent selected from alkyl, aryl, halogen or carbonyl groups; preferably, $R_a$ is an arylcarbonyloxyalkyl or an alkylcarbonyloxyalkyl group substituted by one carboxylate function and one sulfonate function; more preferably, $R_a$ is benzenecarbonyloxyethyl or ethylcarbonyloxyethyl group substituted by one carboxylate function and one sulfonate function;

$R_b$ represents H or methyl; preferably methyl;

X represents O or NH.

In one embodiment, the bifunctional polymerizable monomer of Formula (II) as shown above is such that:
$R_a$ is an acyloxyalkyl group substituted by one carboxylate function and one sulfonate function;
$R_b$ is H;
X represents O or NH.

In one embodiment, the bifunctional polymerizable monomer of Formula (II) as shown above is such that:
$R_a$ is an acyloxyalkyl group substituted by one carboxylate function and one sulfonate function;
$R_b$ is methyl;
X represents NH.

In one embodiment, the bifunctional polymerizable monomer of Formula (II) as shown above is such that:
$R_a$ is an alkyl group substituted by one carboxylate function and one sulfonate function;
$R_b$ is H;
X represents O or NH.

In one embodiment, the bifunctional polymerizable monomer of Formula (II) as shown above is such that:
$R_a$ is an alkyl group substituted by one carboxylate function and one sulfonate function;
$R_b$ is methyl;
X represents O or NH.

One example of preferred compounds of formula (II) is shown below:

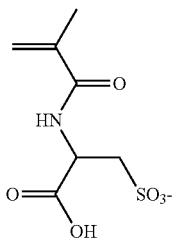

(IIa)

In one embodiment, the bifunctional polymerizable monomer of Formula (II) as shown above is such that:

$R_a$ is an alkylcarbonyloxyalkyl group substituted by one carboxylate function and one sulfonate function; preferably $R_a$ is ethylcarbonyloxyethyl group substituted by one carboxylate function and one sulfonate function;

$R_b$ is H;

X represents O or NH.

Two examples of preferred compounds of formula (II) are shown below:

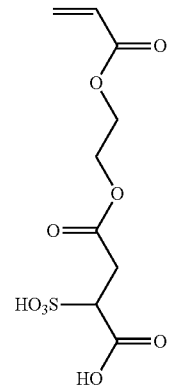

(IIc-1)

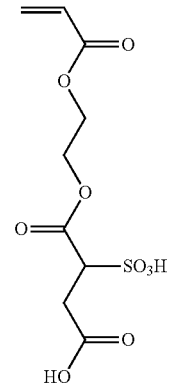

(IIc-2)

In one embodiment, the bifunctional polymerizable monomer of Formula (II) as shown above is such that:

$R_a$ is an alkylcarbonyloxyalkyl group substituted by one carboxylate function and one sulfonate function;

$R_b$ is methyl;

X represents O or NH.

In one preferred embodiment, $R_a$ is not an ethylcarbonyloxyethyl group when X represents O.

In one embodiment, the bifunctional polymerizable monomer of Formula (II) as shown above is such that:

$R_a$ is an arylcarbonyloxyalkyl group substituted by one carboxylate function and one sulfonate function; preferably, $R_a$ is benzenecarbonyloxyethyl group substituted by one carboxylate function and one sulfonate function;

$R_b$ is H;

X represents O or NH.

One example of preferred compounds of formula (II) is shown below:

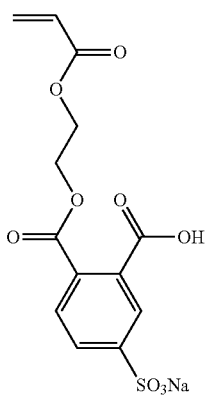

(IIe)

In one embodiment, the bifunctional polymerizable monomer of Formula (II) as shown above is such that:
- $R_a$ is an arylcarbonyloxyalkyl group substituted by one carboxylate function and one sulfonate function; preferably, $R_a$ is benzenecarbonyloxyethyl group substituted by one carboxylate function and one sulfonate function;
- $R_b$ is methyl;
- X represents O or NH.

One example of preferred compounds of formula (II) is shown below:

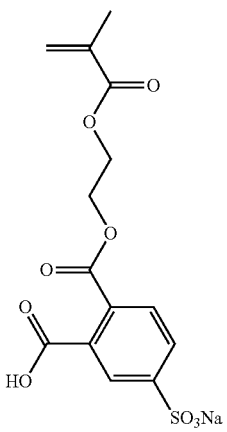

(IId)

In one embodiment, the bifunctional polymerizable monomer of Formula (II) as shown above is such that:
- $R_a$ is an alkylcarbonyloxyaryl group substituted by one carboxylate function and one sulfonate function;
- $R_b$ is H;
- X represents O or NH.

In one embodiment, the bifunctional polymerizable monomer of Formula (II) as shown above is such that:
- $R_a$ is an alkylcarbonyloxyaryl group substituted by one carboxylate function and one sulfonate function;
- $R_b$ is methyl;
- X represents O or NH.

In one embodiment, the bifunctional polymerizable monomer of Formula (II) as shown above is such that:
- $R_a$ is an alkyloxycarbonylalkyl group substituted by one carboxylate function and one sulfonate function;
- $R_b$ is H;
- X represents O or NH.

In one embodiment, the bifunctional polymerizable monomer of Formula (II) as shown above is such that:
- $R_a$ is an alkyloxycarbonylalkyl group substituted by one carboxylate function and one sulfonate function;
- $R_b$ is methyl;
- X represents O or NH.

In one embodiment, the bifunctional polymerizable monomer of Formula (II) as shown above is such that:
- $R_a$ is an aryloxycarbonylalkyl group substituted by one carboxylate function and one sulfonate function;
- $R_b$ is H;
- X represents O or NH.

In one embodiment, the bifunctional polymerizable monomer of Formula (II) as shown above is such that:
- $R_a$ is an aryloxycarbonylalkyl group substituted by one carboxylate function and one sulfonate function;
- $R_b$ is methyl;
- X represents O or NH.

In one embodiment, the bifunctional polymerizable monomer of Formula (II) as shown above is such that:
- $R_a$ is an alkyloxycarbonylaryl group substituted by one carboxylate function and one sulfonate function;
- $R_b$ is H;
- X represents O or NH.

In one embodiment, the bifunctional polymerizable monomer of Formula (II) as shown above is such that:
- $R_a$ is an alkyloxycarbonylaryl group substituted by one carboxylate function and one sulfonate function;
- $R_b$ is methyl;
- X represents O or NH.

According to one embodiment, the adhesion primer used in combination with the polymerizable monomer of Formula (II) may be for example 4-nitrobenzenediazonium.

In an embodiment, the grafted film obtained in the present invention is a copolymer. According to another embodiment, the grafted film obtained in the present invention is a bi-polymer.

According to one embodiment, further polymerizable monomers may be used for the synthesis of the film of the invention such as for example hydroxyethylmethacrylate.

According to one embodiment, the implantable material that is grafted in the present invention is an implantable medical device, preferably an intraocular lens (IOL).

According to another embodiment, the implantable material that is grafted in the present invention comprise at least one surface comprising silicone, polysiloxane, perfluoroalkyl polyether, acrylates such as polymethacrylates, polyacrylates, fluorinated polymethacrylate or polyalkylmethacrylate, polyamides, fluorinated polyolefin, polyhydroxyethylmethacrylate (PHEMA), polyethylene (PE), polypropylene (PP), polyethylene tetraphtalate (PET), polytetrafluoroethylene (PTFE), polyurethanes.

According to a further embodiment, the grafted implantable material of the invention is not cytotoxic.

According to one embodiment, the grafted implantable material of the invention is cytostatic. In other words, the film grafted at the surface of the implantable material of the present invention is a cell antiproliferative film. According to one embodiment, the cell proliferation is reduced from a percentage ranging from 50% to 100%, preferably from 80 to 100%, more preferably from 90 to 100% on the grafted surface of the implantable material of the invention compared to a non-grafted surface of the same material. Cell proliferation may be measured by cell counting using MTT (3-(4,5-dimethylthiazol-2-yl)-2,5-diphenyltetrazolium bromide) colorimetric assay.

According to one embodiment, the grafted implantable material of the invention has antibacterial properties.

According to one embodiment, the grafted implantable material of the invention has cell antiproliferative and/or antibacterial bacterial properties. According to a specific embodiment, the grafted film of the invention prevents the proliferation of cells and/or of bacteria on the surface of the grafted implantable material, especially it prevents the proliferation of lens cells, endothelial cells, keratinocytes or fibroblasts.

According to one embodiment, the grafted film of the present invention has a mechanical resistance to friction strength up to 15 bars. According to one embodiment, the grafted film of the present invention has a mechanical resistance to folding. In the case wherein the implantable material of the invention is an IOL, mechanical resistance to friction and/or folding of the grafted film may be determined by passing the grafted IOL through an insertion cartridge usually used to inject IOLs in the eye and then analyzing the grafted film.

According to an embodiment, the thickness of the grafted film of the invention is ranging from 1 nm to 50 nm, preferably from 2 nm to 20 nm. According to one embodiment, the thickness of the film may be measured by IR spectrometry, using an IR Abacus.

According to one embodiment, the surface of the implantable material is totally covered by the film. According to another embodiment, the surface of the implantable material is partially covered by the film. According to one embodiment, the percentage of the surface of the implantable material that is covered by the film is ranging from 40% to 100%, preferably from 70% to 100% and may be determined by punctual measures in different points of the surface, or by XPS analysis.

According to one embodiment, the film is uniform, i.e. it has a homogenous surface over the entire surface of the grafted implantable material.

Process

The present invention also relates to the process for grafting film comprising carboxylate and sulfonate functions in a 1:1 molar ratio at the surface of an implantable material, preferably an IOL.

According to one embodiment, the process of the invention is a process for simultaneously synthesizing and grafting a film directly onto at least one external surface of an implantable material, comprising a step of contacting, under conditions enabling the formation of radical entities, said external surface with a solution comprising:
  a bifunctional adhesion primer, optionally in presence of one or more polymerizable monomer; or
  an adhesion primer and a bifunctional polymerizable monomer, optionally in presence of one or more further polymerizable monomers.

According to one embodiment, the process of the invention comprises a step of contacting, under conditions enabling the formation of radical entities, the external surface of an implantable material with a solution comprising:
  a bifunctional adhesion primer of Formula (I):

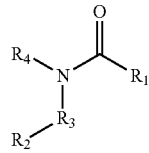

(I)

wherein R1, R2, R3 and R4 are as described herein above;

or
an adhesion primer and a bifunctional polymerizable monomer of Formula (II):

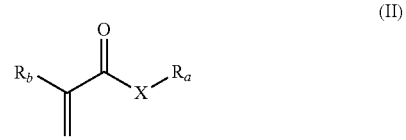

(II)

wherein $R_a$, $R_b$ and X are as described herein above.

In an embodiment, the compound of formula (I) used in the process of the invention is the compound of formula (Ia) as described above.

In an embodiment, the compound of formula (I) used in the process of the invention is the compound of formula (Ib) as described above.

In an embodiment, the compound of formula (II) used in the process of the invention is the compound of formula (IIa) as described above.

In an embodiment, the compound of formula (II) used in the process of the invention is the compound of formula (IIb) as described above.

In an embodiment, the compound of formula (II) used in the process of the invention is the compound of formula (IIc-1) as described above.

In an embodiment, the compound of formula (II) used in the process of the invention is the compound of formula (IIc-2) as described above.

In an embodiment, the compound of formula (II) used in the process of the invention is the compound of formula (IId) as described above.

In an embodiment, the compound of formula (II) used in the process of the invention is the compound of formula (IIe) as described above.

As explained above the grafting reaction first comprises the formation of radicals from the adhesion primer. The radicals' formation may be initiated in presence of a chemical activator and/or physical conditions. According to one embodiment, the conditions enabling the formation of radical entities in the process of the invention may be obtained by using an activator, for example by varying the temperature and/or by adding a chemical activator and/or by using a photochemical and/or radiochemical environment.

According to a first embodiment, the conditions enabling the formation of radical entities may be obtained by adding in the solution used in the process of the present invention a reducing agent as chemical activator. The reducing agent may be for example ascorbic acid, hypophosphoric acid, iron fillings. In the present invention, the adhesion primer comprises a diazonium salt function which enables its chemisorption on the implantable material. When the diazonium salt is reduced to form a radical, there is at the same time a nitrogen release. According to an embodiment, the amount of chemical activator in the solution used in the process of the present invention is ranging from 0.001 M to 0.5 M, preferably from 0.002 M to 0.1 M, more preferably from 0.002 M to 0.01 M. This amount has to be chosen according to the conditions used. Preferably, this amount represents from 0.1 to 20 times of the diazonium salt concentration, as a function of the nature of the chemical activator.

According to second embodiment, the radicals formation is initiated by a physical conditions, for example by using a specific temperature or by illumination at a given wave length. In an embodiment, conditions enabling the formation of radical entities may be obtained by using a temperature ranging from 20° C. to 90° C., preferably from 30° C. to 60° C., more preferably about 40° C.

According to one embodiment, materials that may be grafted by the process of the present invention may have a surface comprising silicone, polysiloxane, perfluoroalkyl polyether, acrylates such as polymethacrylates, polyacrylates, fluorinated polymethacrylate or polyalkylmethacrylate, polyamides, fluorinated polyolefin, polyhydroxyethylmethacrylate (PHEMA), polyethylene (PE), polypropylene (PP), polyethylene tetraphtalate (PET), polytetrafluoroethylene (PTFE), polyurethanes.

According to one embodiment, material that may be grafted by the process of the present invention may be under the form of a constitutive block, of a woven or non-woven textile, it may be full or empty.

The process of the invention comprises contacting under conditions enabling the formation of radical entities as described above, the external surface of an implantable material with a solution comprising:
  a bifunctional adhesion primer of Formula (I); or
  an adhesion primer and a bifunctional polymerizable monomer of Formula (II).

According to a first embodiment, the solution comprises a bifunctional adhesion primer of Formula (I). In this embodiment, the solution may optionally further comprise one or more polymerizable monomer, leading to a cofilm.

According to a second embodiment, the solution comprises an adhesion primer and a bifunctional polymerizable monomer of Formula (II). In this embodiment, the solution may optionally further comprise one or more polymerizable monomer.

According to one embodiment, the solution used in the process of the invention is an acidic solution. In this embodiment, the pH of the solution is ranging from 1 to 7, preferably from 2 to 5, more preferably less than or equal to 3.

According to one embodiment, the solvent of the solution used in the process of the invention is a protic solvent. In an embodiment, the protic solvent is chosen from the group comprising water, deionized water, distilled water, acidified or not, acetic acids, hydroxylated solvents such as methanol and ethanol, low-molecular-weight liquid glycols such as ethyleneglycol and mixtures thereof. In a preferred embodiment, the protic solvent is water, deionised water or distilled water, acidified or not. According to another embodiment, the solvent of the solution used in the process of the invention is an aprotic solvent, preferably acetonitrile, dimethylformamide, dimethylsulfoxide or a mixture thereof. Alternatively, the solvent of the solution used in the process of the invention is a mixture of a protic solvent or a mixture of protic solvents together with an aprotic solvent or a mixture of aprotic solvents.

In an embodiment, the solvent of the solution used in the process of the invention does not contain any carboxylate or sulfonate function.

According to a very preferred embodiment, the adhesion primers used in the process of the invention are diazonium salts. By definition, the adhesion primer of Formula (I) comprises a diazonium salt group on R2. According to a preferred embodiment, the adhesion primer used in combination with the monomer of Formula (II) may be for example a 4-nitrobenzene diazonium salt.

The adhesion primer of Formula (I) or the one used in combination with the monomer of Formula (II), may either be directly introduced in the solution used in the process of the present invention or be prepared in situ in the latter. When the adhesion primer is prepared in situ, the reaction is referred to as a "one-pot" reaction.

According to a first embodiment, the adhesion primer under the form of a diazonium salt is directly introduced in the solution used in the process of the present invention. In one embodiment, the diazonium salt may have been separately obtained by reacting an aniline derivative (i.e. an aromatic primary amine) with boron trifluoride diethyl etherate in presence of tert-butyl nitrite and isolating the resulting diazonium salt. The skilled artisan may also refer to other known methods to synthesize and isolate diazonium salts in order to obtain the adhesion primers.

According to a second embodiment, the adhesion primer under the form of a diazonium salt is prepared in situ in the solution used in the process of the invention. The diazonium salt may be obtained by reacting an aniline derivative (i.e. an aromatic primary amine) with $NaNO_2$ in an acidic medium. For detailed experimental method that may be used for such an in situ preparation, one skilled artisan can refer to Lyskawa and Belanger, Chem. Mater. 18, 2006, 4755-4763. The grafting will then be performed directly in the solution used for the preparation of the diazonium salt.

According to one embodiment, the amount of adhesion primer, in the solution used in the process of the present invention may vary as desired by the experimenter. Variations of this amount may participate to the control of the thickness of the grafted film. In order to obtain a film grafted on the quite entire surface of the material, it is necessary to use a minimum amount of adhesion primer which may be estimated by molecular size calculation together with the size of the surface to be grafted. According to one embodiment, the concentration of adhesion primer in the solution used in the process of the present invention is ranging from 0.005 M to 0.2 M, preferably from 0.01 M to 0.1 M, more preferably from 0.02 to 0.08 M, more preferably about 0.05 M.

According to a very preferred embodiment, the radically polymerizable monomers which may be used in the process of the invention are vinylic monomers. By definition, the polymerizable monomer of Formula (II) is vinylic. According to a preferred embodiment, the polymerizable monomer which may be optionally be further added for the synthesis of the grafted material of the invention are for example styrene, acrylate or methacrylate, acrylamide or methacrylamide.

The amount of polymerizable monomer in the solution used in the process of the present invention may vary as desired by the experimenter. Variations of this amount may participate to the control of the thickness of the grafted film. According to one embodiment, the concentration of polymerizable monomer in the solution used in the process of the present invention is ranging from 0.05 M to 5 M, preferably from 0.1 M to 2 M, more preferably from 0.2 M to 1 M.

According to an embodiment, a surfactant may be added in the solution used in the process of the present invention. According to the present invention, a surfactant is a molecule comprising a lipophilic moiety (apolar) and a hydrophilic moiety (polar). Without willing to be linked by any theory, it is Applicant opinion that the presence of a surfactant promotes radicals formation by isolating them in micelles and therefore promotes copolymerization-like reaction. Among surfactants that may be used according to the present invention, it is possible to mention:
  i) anionic surfactants, in which the hydrophilic part is negatively charged, such as for example, sodium dodecylsulfate, sodium palmitate, sodium stearate, sodium myristate, di(2-ethylhexyl) sodium; sulfosuccinate;

ii) cationic surfactants, in which the hydrophilic part is positively charged, such as for example ammonium tetradecyl trimethyl bromide (TTAB), alkyl-pyridinium halides having a C1-C18 aliphatic chain and the alkylammonium halides;
iii) zwitterionic surfactants which are neutral compounds having formal electrical charges with similar value and opposite sign, such as for example N,N-dimethyldocecyl ammonium sodium butanoate, dimethyldodecyl ammonium sodium propanoate, and the amino acids;
iv) amphoteric surfactants, which are compounds that simultaneously behave like an acid or like a base depending on the medium in which they are placed; these compounds may have a zwitterionic nature, amino acids are specific example of this family;
v) neutral surfactants, also called non-ionic surfactants, wherein the surfactant properties, in particular hydrophobicity, are provided by uncharged functional groups, such as for example polyethers like the polyethoxylated surfactants such as e.g. polyethylene glycol lauryl ether (POE23 or Brij(R) 35), the polyols (surfactants derived from sugars), in particular the glucose alkylates such as e.g., glucose hexanate.

In an embodiment, the surfactant used in the process of the invention does not contain any carboxylate or sulfonate function. In an embodiment, the surfactant does not contain any aromatic cycle.

The process of the present invention is carried out under gentle and non-destructive conditions, preferably under normal conditions of temperature and pressure.

According to one embodiment, the material to be grafted is immersed the solution used in the process of the invention. According to another embodiment, the solution is sprayed onto the surface of the material.

According to one embodiment, the reaction is performed during a period of time ranging from 5 min to 90 min, preferably from 10 min to 30 min.

According to an embodiment, the reaction time may be adjusted. This adjustment of the time of exposure of the surface of the material to the solution makes it possible to control the thickness of the film that is obtained.

According to one embodiment, the efficiency of the grafting may be determined by any suitable means of analysis, especially by X photoelectron spectroscopy (XPS) measurements or measure of contact angles. According to one embodiment, XPS analysis may be performed using a Kratos Axis Ultra apparatus. According to one embodiment, contact angle measure may be performed using an Apollo Instruments apparatus.

According to an embodiment, the process of the present invention comprises a preliminary step of pre-treating the surface of the material to be grafted. In this embodiment, the pre-treatment comprises cleaning the surface to be grafted, for example by ultrasound treatment in water and/or in an organic solvent such as cyclohexane, ethanol. Prior to grafting, the pre-treated surface may be further rinsed with water, preferably deionized water.

According to another embodiment, the surface of the material may be pre-treated by an acidic treatment, a basic treatment or an oxido-reductive treatment.

According to an embodiment, the process of the present invention comprises a further step of post-treatment. This further step comprises treating the grafted material in water at a temperature ranging from 60 to 100° C., preferably about 100° C. for a period of time ranging from 1 to 10, preferably about 5 min, optionally followed by rinsing in a solvent such as ethanol. Without willing to be linked by any theory, it is Applicant's opinion that this post-treatment may help eliminating the non-grafted compounds. This step may-therefore prevent from heavy releasing of non-grafted compounds once the grafted implantable material is implanted.

Use of Grafted Implantable Materials

The present invention also relates to the use of the grafted implantable material of the invention to manufacture an antiproliferative and/or antibacterial implantable medical device, preferably an antiproliferative and/or antibacterial IOL.

Implantable medical devices that may be grafted by the process of the present invention are for example implants, intraocular lenses (IOLs), stents, catheters, implants for abdominal surgery, vascular prostheses, artificial limbs, preferably IOLs.

According to one embodiment, implantable medical devices which may be grafted by the process of the present invention are non-metallic.

According to one embodiment, the grafted implantable material of the invention is used to manufacture an antiproliferative and/or antibacterial IOL. In one aspect of this embodiment, the implantable material to be grafted by the process of the present invention is hydrophilic or hydrophobic. In another aspect of this embodiment, the implantable material to be grafted by the process of the present invention is an IOL, preferably a commercially available IOL.

The present invention also relates to a kit comprising a grafted implantable material according to the present invention and an inserting and/or implantation device.

According to one embodiment, the kit of the invention comprises an intraocular lens (IOL) grafted according to the invention and an IOL-inserting device.

The present invention also relates to an intraocular lens having at least one external surface grafted with a film comprising carboxylate and sulfonate functions in a 1:1 molar ratio, wherein the film is produced by the process of the invention.

Compounds of Formula (I)

The present invention also relates to compounds of Formula (I)

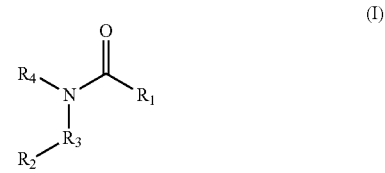

wherein R1, R2, R3 and R4 are as described herein above;

According to a specific embodiment, precursors of compounds of Formula (I) are for Formula prec-Ia and prec-Ib:

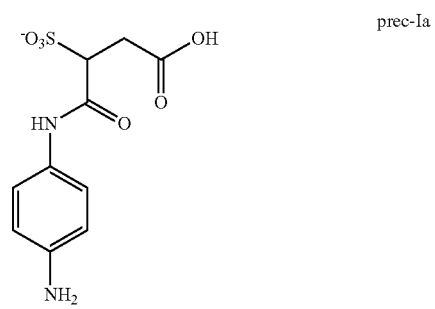

-continued prec-Ib

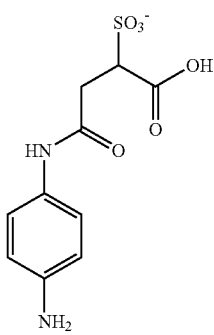

In one embodiment, Ia and Ib are formed in situ from their precursors prec-Ia and prec-Ib in presence of a nitrite, preferably NaNO2, $KNO_2$, $Ca(NO_2)_2$.

In one embodiment, compounds of Formulae prec-(Ia) and prec-(Ib) may be synthesized by Method A or Method B as detailed in the experimental part below.

Compounds of Formula (II)

The present invention also relates to compounds of Formula (II)

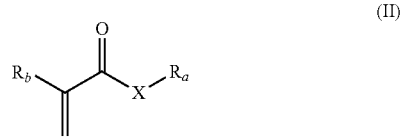

wherein $R_a$, $R_b$ and X are as described herein above;

for use as an antiproliferative and/or antibacterial agent.

Advantage

Using a bifunctional source, which carries both sulfonate -and carboxylate functions, presents a strong advantage: the 1:1 ratio may be assessed as soon as the presence of the film is assessed. An analysis revealing the presence of sulfur atoms (good marker in IR and XPS and absent in implantable material, especially in IOL implantable materials) shall thus result in evidencing, in one step and in a glance, the grafting of the molecule and the 1:1 ratio. This invention may thus include a quality control process step, wherein the presence of the film is assessed by any suitable technique, especially but not limitatively by searching the sulfur marker in IR or XPS.

EXAMPLES

Figure 1:
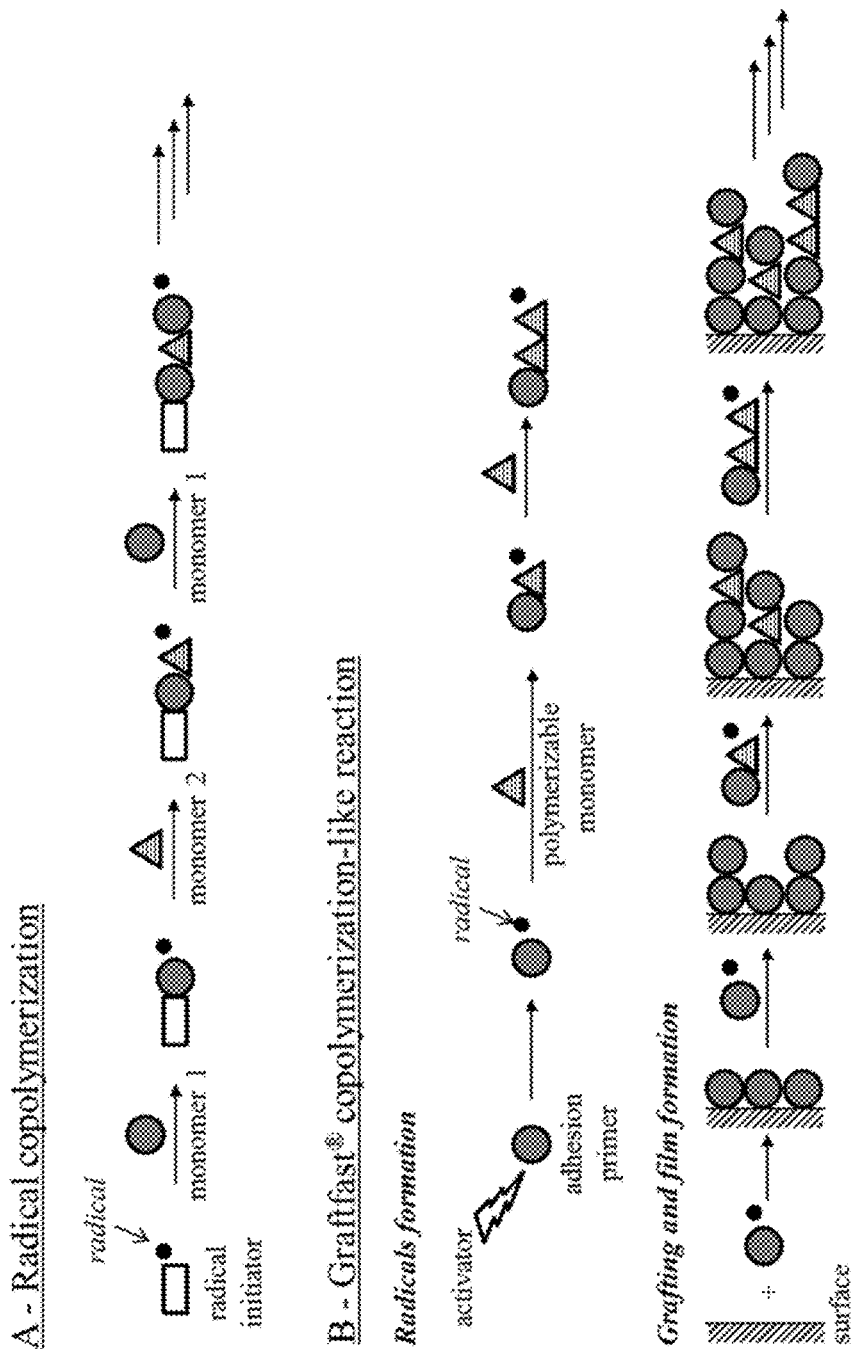
FIG. 1 is a scheme representing the principles of radical copolymerization and of Graftfast® copolymerization-like reaction.
Figure 2:
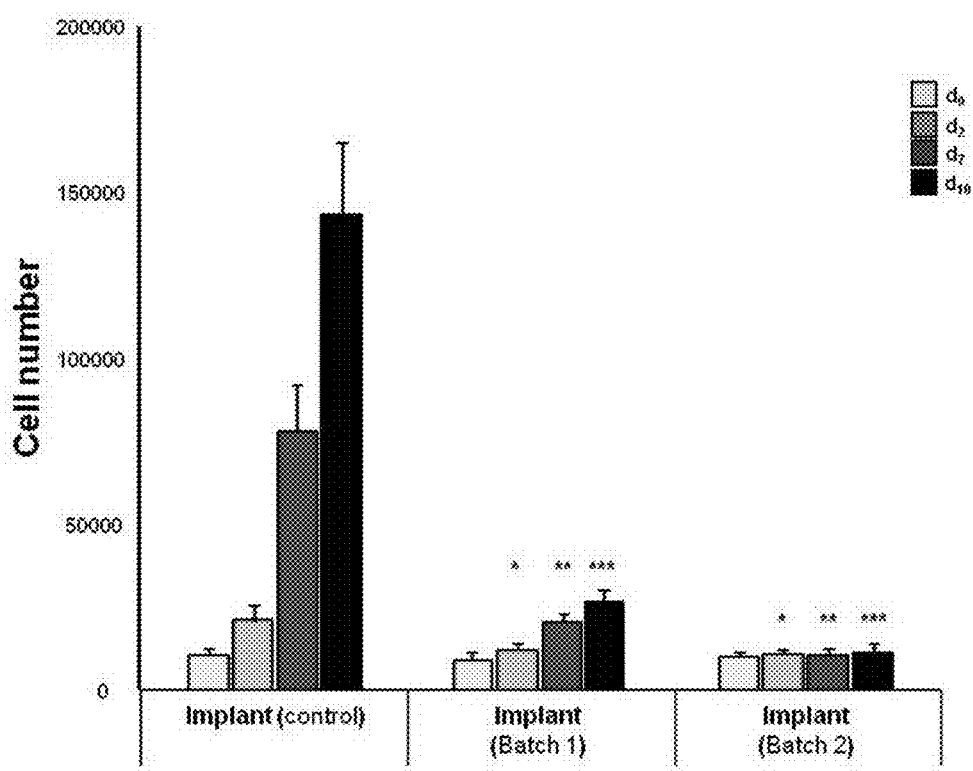
FIG. 2 is a graph representing the number of LEC cells present at the surface of materials grafted according to the present invention (Statistics: Control vs Test; p<0.001; *p<0.0001).

The present invention is further illustrated by the following examples.

Materials

All standard chemicals were purchased from Sigma Aldrich.

The following examples were performed in glass cell and otherwise stated they were conducted in normal conditions of pressure in ambient air.

1. Synthesis of Adhesion Primer of Formula (I)

The synthesis of 1-((4-aminophenyl)amino)-3-carboxy-1-oxopropane-2-sulfonate prec-Ia and et 3-((4-aminophenyl)amino)-1-carboxy-3-oxopropane-1-sulfonate prec-Ib was performed using two different routes of synthesis.

1.1. Method A

Scheme A: Synthesis of compound prec-Ia and prec-Ib according to Method A.

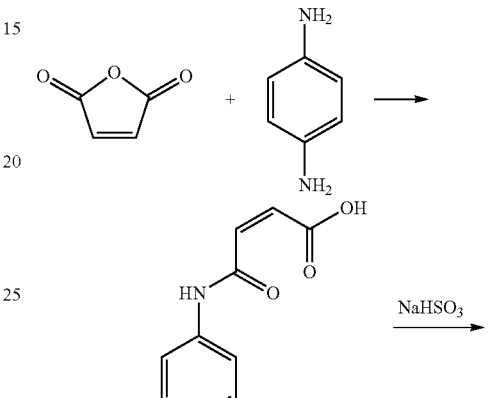

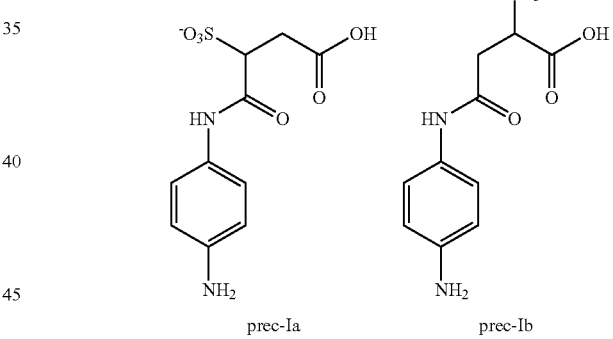

prec-Ia    prec-Ib

Step A1. Synthesis of (Z)-4-((4-aminophenyl)amino)-4-oxobut-2-enoic Acid 1

During this first step, maleic anhydride (5,4 g, 55 mmol), dissolved in 100 mL of an aprotic solvent (DCM, THF, acetonitrile), is added dropwise in a solution of p-phenylene diamine (6.2 g, 57.4 mmol) in 200 mL of an aprotic solvent, at room temperature under vigourous stirring. The resulting solution is stirred overnight. The solution is filtrated to provide a crude yellow product which is with diethylether and dried under reduced pressure, affording a 92% yield.

RMN $^1$H (400 MHz, DMSO-d6) δ (ppm/TMS): 3.32 (bs, 3H $NH_2$—($C_6H_5$)—NH—), 6.27 (d, 1H, NH—(C=O)—CH=CH—COOH), 6.47 (d, 1H, NH—(C=O)—CH=CH—COOH), 6.52 (d, 2H, $C_6H_4$), 7.28 (d, 2H, $C_6H_4$), 10.46 (s, 1H, COOH).

Step A2. Sulfonation Leading to -prec-Ia and prec-Ib (Z)-4-((4-aminophenyl)amino)-4-oxobut-2-enoic acid (5 g, 24 mmol) is dissolved in 100 mL propan-2-ol at 50° C. Sulfite sodium salt (4 g, 31 mmol) in water is added dropwise to the solution under vigourous stirring. The mixture is heated to 82° C. overnight. The final mixture is filtered to provide a white powder, which is washed abundantly with warm ethanol and finally dried under reduced pressure. The final yield is over 90%.

RMN $^1$H (400 MHz, DMSO-d6) δ (ppm/TMS): 2.65-2.94 (m, 2H, CH(SO$_3$)—CH$_2$), 3.65 (dd, 1H CH(SO$_3$)—CH$_2$), 6.44 (d, 2H, C$_6$H$_4$), 7.16 (d, 2H, C$_6$H$_4$), 9.57 (s, 1H, COOH).

1.2. Method B

Scheme B: Synthesis of compound prec-Ia and prec-Ib according to Method B.

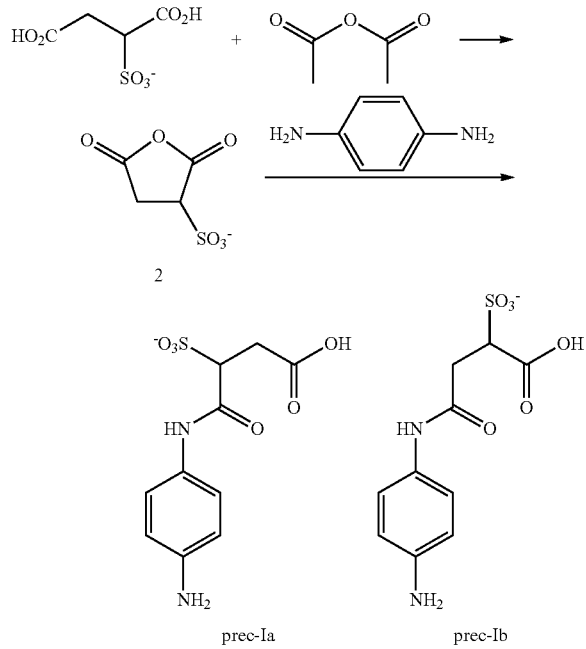

Step B1. Synthesis of 2,5-dioxotetrahydrofuran-3-sulfonate 2

Acetic anhydride (60 mL) is poured in large excess (8:1) in a reactor containing sulfosuccinic acid (15 ml, 70% w in H$_2$O) and the mixture is stirred during 2 hours at 80° C. The solvents are removed under heating and reduced pressure to afford a dark red oil, which is used directly in step 2 without any further purification.

RMN $^1$H (400 MHz, DMSO-d6) δ (ppm/TMS): 2.65-2.94 (m, 2H, CH(SO$_3$)—CH$_2$), 3.65 (dd, 1H CH(SO$_3$)—CH$_2$).

Step B2. Synthesis of prec-Ia and prec-Ib

The crude sulfosuccinic anhydride (15 g, 84 mmol) diluted in an aprotic solvent (THF) is added dropwise to a solution of p-phenylene diamine (16 g, 89 mmol) also dissolved in an aprotic solvent (THF). The reaction is stirred overnight and the solution is finally filtrated to provide a white/light brown powder, which is washed with ethanol, diethylether and dried under reduced pressure. Yield is about 90%.

RMN $^1$H (400 MHz, DMSO-d6) δ (ppm/TMS): 2.65-2.94 (m, 2H, CH(SO$_3$)—CH$_2$), 3.65 (dd, 1H CH(SO$_3$)—CH$_2$), 6.44 (d, 2H, C$_6$H$_4$), 7.16 (d, 2H, C$_6$H$_4$), 9.57 (s, 1H, COOH).

2. Synthesis of Polymerizable Monomer of Formula (II)

2.1. Synthesis of 2-carboxy-2-methacrylamidoethanesulfonate (IIa)

The synthesis of 2-carboxy-2-methacrylamidoethanesulfonate IIa was performed according to Method C (scheme C):

Scheme C: Synthesis of compound IIa according to Method C.

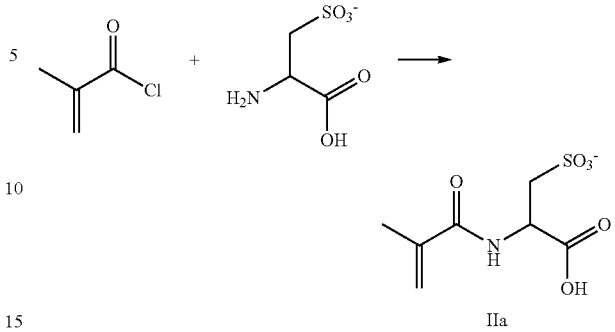

Methacryloyl chloride (10 mL, 89 mmol) is added dropwise to a stirred solution of cysteic acid (18.3 g, 98 mmol) in dimethylformamide (200 mL), at 4° C. during 4 h. At the end, the crude product is separated by filtration and washed with THF. The final product is dried under reduced pressure to afford a yield of 76%.

RMN $^1$H (400 MHz, DMSO-d6) δ (ppm/TMS): RMN $^1$H (400 MHz, D$_2$O) δ (ppm/TMS): 1.85 (s, 3H, CH$_2$=C(CH$_3$)), 3.44-3.56 (m, 2H, $^-$O$_3$S—CH$_2$), 4.48 (m, 1H, (C=O)NH—CH—COOH) 5.38 (d, 1H, CH$_2$=C(CH$_3$)), 5.72 (d, 1H, CH$_2$=C(CH$_3$)).

The synthesis of 2-carboxy-2-methacrylamidoethanesulfonate IIa may also be performed according to Method D, using an activated ester (scheme D):

Scheme D: Synthesis of compound IIa according to Method D.

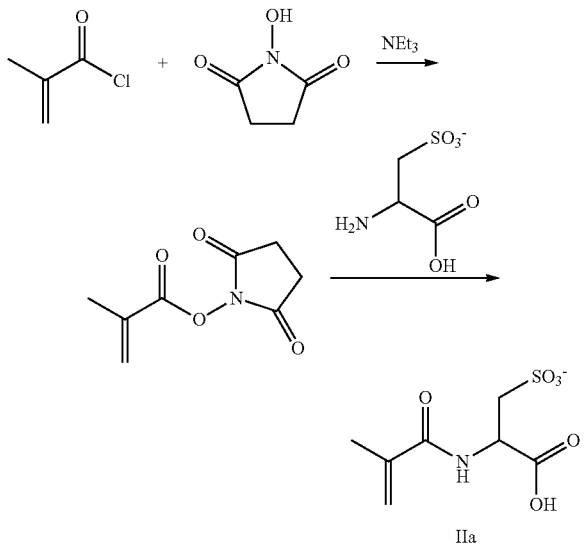

Step D1. Synthesis of N-methacryloyloxysuccinimide (NMAS)

Methacryloyl chloride (10 mL, 89 mmol) was added dropwise to a stirred solution of N-hydroxysuccinimide (11 g, 98 mmol) and triethylamine (13 mL, 98 mmol) in chloroform at 0° C. After stirring for 4 h at 0° C., the reaction mixture was washed with ice-cold saturated sodium bicarbonate solution four times and dried on MgSO4 overnight. Then, the solution was filtered and chloroform was removed by evaporation. Yield ca. 75%.

RMN $^1$H (400 MHz, DMSO-d6) δ (ppm/TMS): 1.95 (s, 3H, CH$_2$=C(CH$_3$), 2.80 (s, 4H, —(C=O)—CH$_2$—CH$_2$—(C=O)—), 5.68; 6.28 (d, CH$_2$=C(CH$_3$)).

Step D2. Synthesis of 2-carboxy-2-methacrylamidoethanesulfonate

A solution of cysteic acid in water is added dropwise to a stirred solution of NMAS in DMF at room temperature. The solution was allowed to stir overnight and then the pH of the solution was lowered with concentrated hydrochloric acid. The final mixture is filtered to provide a white powder which is washed with diethylether and dried under reduced pressure. Yield is about 85%.

RMN $^1$H (400 MHz, DMSO-d6) δ (ppm/TMS): RMN $^1$H (400 MHz, D$_2$O) δ (ppm/TMS): 1.85 (s, 3H, CH$_2$=C(CH$_3$)), 3.44-3.56 (m, 2H, $^-$O$_3$S—CH$_2$), 4.48 (m, 1H, (C=O)NH—CH—COOH) 5.38 (d, 1H, CH$_2$=C(CH$_3$)), 5.72 (d, 1H, CH$_2$=C(CH$_3$)).

2.2. Synthesis of 4-[(2-[(2-methyl-1-oxo-2-ethenyl)oxy]ethyl]ester of Sulfobutanoic Acid (IIc-1 and IIc-2)

The synthesis of the 4-[(2-[(2-methyl-1-oxo-2-ethenyl)oxy]ethyl]ester of sulfobutanoic acid was performed according to the method E:

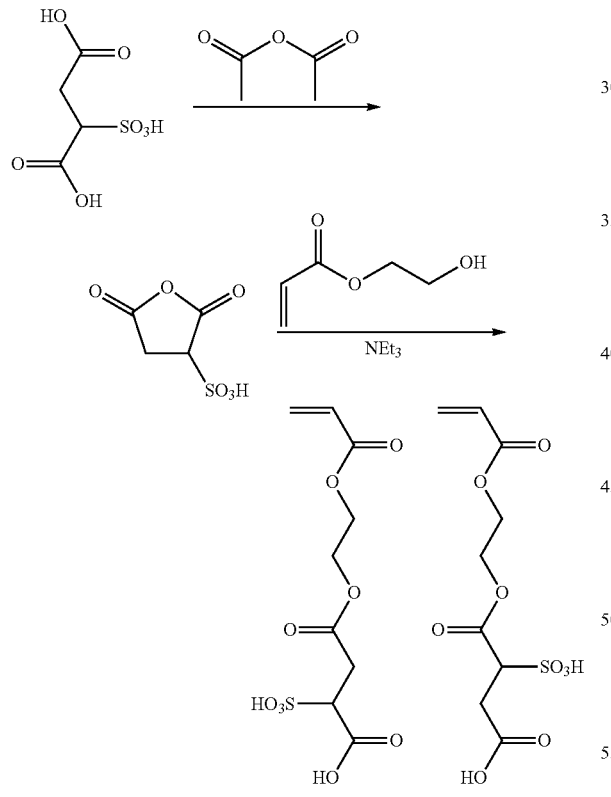

Step E1. Synthesis of the sulfosuccinic snhydride

Sulfosuccinic acid (28 g, 127 mmol) was poured into acetic anhydride (35 mL, 370 mmol) and the slurry was stirred during 4 h at 80° C. The mixture is cooled down and filtrated. The crude solid is washed first with acetic acid during 30 min and then with diethyl ether. The white solid is dried under vacuum and the anhydride formation is controlled by FTIR (C=O stretching modes at 1770 and 1860 cm$^{-1}$).

Step E2. Synthesis of 4-[2-[(2-methyl-1-oxo-2-ethenyl)oxy]ethyl]ester of sulfobutanoic acid Sulfosuccinic anhydride (5 g, 24 mmol), Hydroxyethyl acrylate (10 mL, 87 mmol) and triethylamine (10 mL, 72 mmol) are stirred together at room temperature during 16 h. The mixture is filtrated and the crude product is precipitated in an acetone/diethyl ether 1:1 solution. The solution is filtrate and the white solid is dried under vacuum.

RMN $^1$H (D$_2$O, δ (ppm)/TMS): 6.50 (dd, 1H, CH$_2$=CH—), 6.25 (dd, 1H, CH$_2$=CH), 6.04 (dd, 1H, CH$_2$=CH), 4.55-4.35 (m, 4H, —CH$_2$—CH$_2$—), 4.20-3.97 (dd×2, 1H, —CH(SO$_3^-$)—), 3.12-2.78 (m, 2H, —CH(SO$_3^-$)—CH$_2$—).

2.3. Synthesis of the 4-[2-[(2-methyl-1-oxo-2-propenyl)oxy]ethyl]ester of 4-sulfophthalic Acid (IId)

The synthesis of the 4-[2-[(2-methyl-1-oxo-2-propenyl)oxy]ethyl]ester of 4-sulfophthalic acid was performed according to the method F.

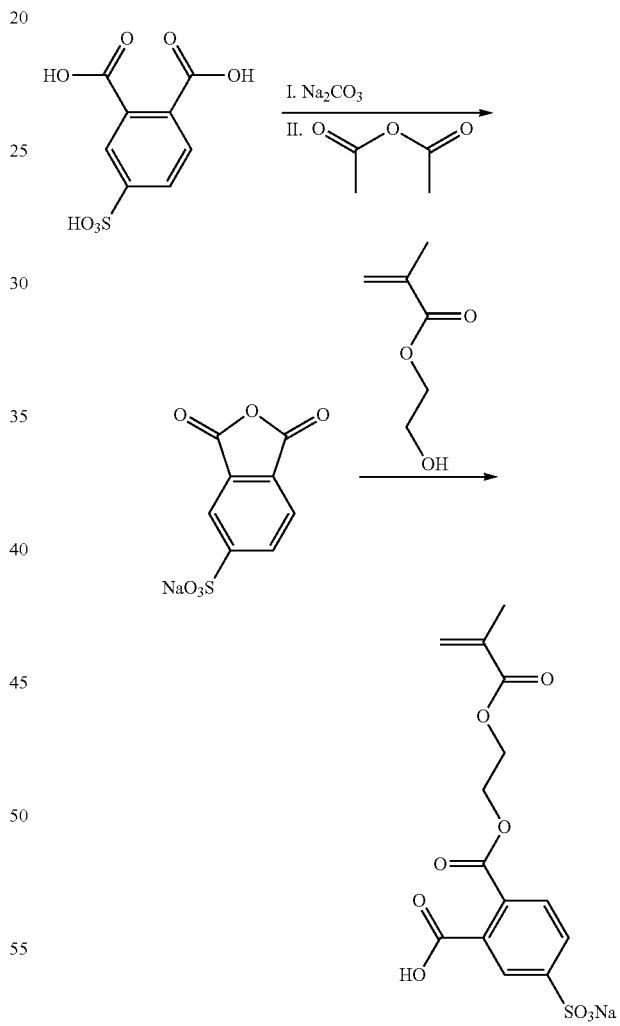

Step F1. Synthesis of the 4-sulfophthalic Anhydride Sodium Salt

First, sodium carbonate (6.26 g, 59 mmol) is added to the 4-sulfophthalic acid (15 mL, 39 mmol, 50% wt in water). The 4-sulfophthalic acid trisodium salt forms a white solid, which is washed in 100 mL acetone, filtrated and dried under vacuum. A part of the white solid, (4.6 g, 14 mmol) is stirred with acetic anhydride (40 mL, 423 mmol) at 80° C. during 4 h. The mixture is cooled down and filtrated. The crude solid is washed first with acetic acid during 30min and then with diethyl ether. The white solid is dried under vacuum and the anhydride formation is controlled by FTIR (C=O stretching modes at 1770 and 1860 cm$^{-1}$).

Step F2. Synthesis of the 4-[2-[(2-methyl-1-oxo-2-propenyl)oxy]ethyl]ester of 4-sulfophthalic acid 4-sulfophthalic anhydride sodium salt (5 g, 20 mmol), Hydroxyethyl methacrylate (10 mL, 82 mmol) and triethylamine (10 mL, 72 mmol) are stirred together at room temperature during 16 h. The mixture is filtrated and the crude product is precipitated in an acetone/diethyl ether 1:1 solution. The solution is filtrate and the white solid is dried under vacuum. The resulting white solid is dissolved into a small amount of water, and a 0.1 mol/L NaOH solution is slowly added to reach pH 9. The solution is poured into an acetone/diethyl ether 1:1 solution to form a white solid, which is isolate and dried under vacuum.

RMN $^1$H (D$_2$O, δ (ppm)/TMS): 8.20-7.50 (m, 3H, aryl group), 6.13 (s, 1H, CH$_2$=C—), 5.69 (s, 1H, CH$_2$=C), 4.65-4.45 (m, 4H, —CH$_2$—CH$_2$—), 1,90 (s, 3H, CH$_3$—C—).

2.4. Synthesis of the 4-[2-[(2-methyl-1-oxo-2-ethenyl)oxy]ethyl]ester of 4-sulfophthalic Acid was Performed According to the Method G (IIe)

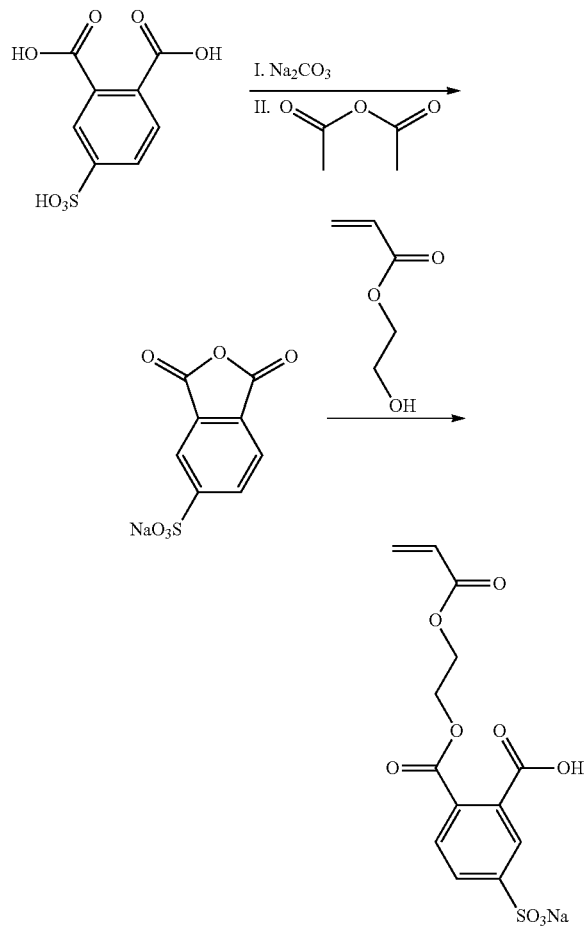

Step G1. Synthesis of the 4-sulfophthalic anhydride sodium salt

First, sodium carbonate (6.26 g, 59 mmol) is added to the 4-sulfophthalic acid (15 mL, 39 mmol, 50% wt in water). The 4-sulfophthalic acid trisodium salt forms a white solid, which is washed in 100 mL acetone, filtrated and dried under vacuum. A part of the white solid, (4.6 g, 14 mmol) is stirred with acetic anhydride (40 mL, 423mmol) at 80° C. during 4 h. The mixture is cooled down and filtrated. The crude solid is washed first with acetic acid during 30 min and then with diethyl ether. The white solid is dried under vacuum and the anhydride formation is controlled by FTIR (C=O stretching modes at 1770 and 1860 cm$^{-1}$).

Step G2. Synthesis of the 4-[2-[(2-methyl-1-oxo-2-ethenyl)oxy]ethyl]ester of 4-sulfophthalic acid 4-sulfophthalic anhydride sodium salt (5 g, 20 mmol), Hydroxyethyl acrylate (10 mL, 87 mmol) and triethylamine (10 mL, 72 mmol) are stirred together at room temperature during 16 h. The mixture is filtrated and the crude product is precipitated in an acetone/diethyl ether 1:1 solution. The solution is filtrate and the white solid is dried under vacuum. The resulting white solid is dissolved into a small amount of water, and a 0.1 mol/L NaOH solution is slowly added to reach pH 9. The solution is poured into an acetone/diethyl ether 1:1 solution to form a white solid, which is isolate and dried under vacuum.

RMN $^1$H (D$_2$O, δ (ppm)/TMS): 8.20-7.50 (m, 3H, aryl group), 6.45 (dd, 1H, CH$_2$=CH—), 6.23 (dd, 1H, CH$_2$=CH), 5.98 (dd, 1H, CH$_2$=CH), 4.65-4.45 (m, 4H, —CH$_2$—CH$_2$—).

3. IOL Grafting

Hydrophilic plots grafting

Cylinders of polyhydroxyethyl methacrylate (PHEMA) having a diameter of 13 mm and a high of 3 mm were used for grafting tests. These cylinders are precursors of hydrophilic intraocular implants.

3.1. Diazonium Salt One-Pot Synthesis

The grafting of 20 PHEMA cylinders was tested in presence of Hydroxyethylmethacrylate (HEMA) 4-((4-aminophenyl)amino)-4-oxo-2-sulfo-butanoic acid and 4-((4-aminophenyl)amino)-4-oxo-3-sulfo-butanoic acid (noticed as compounds prec-Ia and prec-Ib) with the one pot synthesis of the corresponding diazonium salt.

Pre-Treatment

The PHEMA cylinders were first polished with colloidal alumina powder to a Ra=0.02 μm roughness. The PHEMA cylinder were placed in a beaker, covered by deionized water and treated by ultrasonic for 2×10 minute. The cylinders were then covered with ethanol and sonicated again for 10 min. Finally they are dried under nitrogen flux.

HEMA (0.25 mol/L) and compounds prec-Ia and prec-Ib (0.05 mol/L) are mixed in deionized water, acidified with HCl (pH=1). NaNO$_2$ (0.05 mol/L) is added dropwise under mechanical agitation. PHEMA cylinders are placed in the solution and ascorbic acid (0.01 mol/L) is added in the mixture. The reaction is let for 1 hour. The PHEMA cylinders are then sonicated in a deionized water bath and an ethanol bath for 15 minutes, before being dried under a nitrogen flux and dried at 100° C. for 10 minutes.

3.2. Diazonium Salt One-Pot Synthesis Without Monomeric Dilution

The grafting of two series of 20 PHEMA cylinders was tested in presence of 4-((4-aminophenyl)amino)-4-oxo-2-sulfo-butanoic acid and 4-((4-aminophenyl)amino)-4-oxo-3-sulfo-butanoic acid (noticed as compounds prec-Ia and prec-Ib) with the one pot synthesis of the corresponding diazonium salt.

Pre-Treatment

The PHEMA cylinders were first polished with colloidal alumina powder to a Ra=0.02 μroughness. The PHEMA cylinder were placed in a beaker, covered by deionized water and treated by ultrasonic for 2×10 minute. The cylinders were then covered with ethanol and sonicated again for 10 min. Finally they are dried under nitrogen flux.

Grafting

Compounds prec-Ia and prec-Ib (0.05 mol/L) are mixed in deionized water, acidified with HCl (pH=1). NaNO$_2$ (0.05 mol/L) is added dropwise under mechanical agitation. PHEMA cylinders are placed in the solution and ascorbic acid (0.01 mol/L) is added in the mixture. The reaction is let for 1 hour. The PHEMA cylinders are then sonicated in a deionized water bath and an ethanol bath for 15 minutes, before being dried under a nitrogen flux and dried at 100° C. for 10 minutes.

4. Cellular Proliferation Assessment 4.1. Method

Study of the growth of human lens cells (LEC) onto grafted material obtained according to the methods described at paragraphs 3.1 and 3.2 above.

Human eye lens epithelial cells (LEC, CRL-11421,ATCC, USA) are seeded onto grafted implants in 24-well microplates at a rate of 20 000 cells per well in RPMI medium (VWR, France). After 2, 7 and 10 days of culture, LEC cells are counted using the MTT colorimetric assay. Control corresponds to LEC culture onto non-grafted material.

Batch 1 are plots grafted with compounds Ia and Ib.

Batch 2 are plots grafted with compounds Ia and Ib in presence of HEMA.

4.2. Results

A general observation is that human lens cells do not proliferate onto grafted materials and that grafted materials of the invention have cytostatic but no cytotoxic activities.

The invention claimed is:

1. An implantable material having at least one external surface grafted with a film comprising carboxylate and sulfonate functions wherein the film is simultaneously synthesized and grafted directly on said external surface by radical reaction of:
a bifunctional adhesion primer of Formula (I)

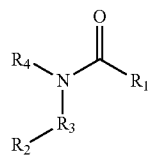

wherein
R$_1$ represents a group substituted by one carboxylate function and one sulfonate function, said group being selected from linear or branched alkyl, aryl, or heteroaryl; said groups being optionally substituted by one or more substituent selected from alkyl, aryl, halogen or carbonyl;
R$_2$ represents an aryl or heteroaryl group substituted by at least one diazonium salt group and optionally further substituted by one or more substituent selected from alkyl, aryl or halogen;
R$_3$ is a bond or represents or a linear or branched C1-C3 alkyl group, optionally substituted by one or more substituent selected from alkyl, aryl, heteroaryl, halogen or nitro;
R$_4$ represents a hydrogen atom or a group selected from alkyl, aryl, heteroaryl or alkylcarbonyl.

2. The implantable material according to claim 1, wherein the film is simultaneously synthesized and grafted directly on the external surface by radical chemisorption and polymerization of a bifunctional adhesion primer of Formula (I)

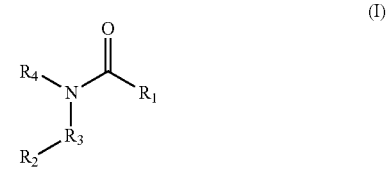

wherein
R$_1$ represents a group substituted by one carboxylate function and one sulfonate function, said group being selected from a C2-C4 alkyl;
R$_2$ represents a benzodiazonium group;
R$_3$ is a bond;
R$_4$ represents a hydrogen atom.

3. The implantable material according to claim 1, wherein the thickness of the film is from 1 nm to 50 nm.

4. A process for simultaneously synthesizing and grafting a film directly onto at least one external surface of an implantable material, comprising a step of contacting, under conditions enabling the formation of radical entities, said external surface with a solution comprising:
a bifunctional adhesion primer of Formula (I)

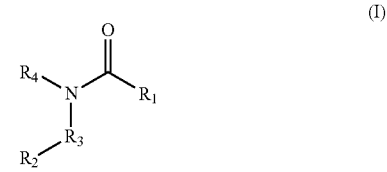

wherein
R$_1$ represents a group substituted by one carboxylate function and one sulfonate function, said group being selected from linear or branched alkyl, aryl, or heteroaryl; said groups being optionally substituted by one or more substituent selected from alkyl, aryl, halogen or carbonyl;
R$_2$ represents an aryl or heteroaryl group substituted by at least one diazonium salt group and optionally further substituted by one or more substituent selected from alkyl, aryl or halogen;
R$_3$ is a bond or represents a linear or branched C1-C3 alkyl group, optionally substituted by one or more substituent selected from alkyl, aryl, heteroaryl, halogen or nitro;
R$_4$ represents a hydrogen atom or a group selected from alkyl, aryl, heteroaryl or alkylcarbonyl.

5. The process according to claim 4, wherein the solution comprises water, deionized water, distilled water, acidified or not, acetic acid, hydroxylated solvents, low-molecular-weight liquid glycols and mixtures thereof.

6. The process according to claim 4, wherein the conditions enabling the formation of radical entities comprise the use of a reducing agent.

7. The process according to claim 4, wherein the solution comprises a precursor of a bifunctional adhesion primer of Formula (I) selected from:

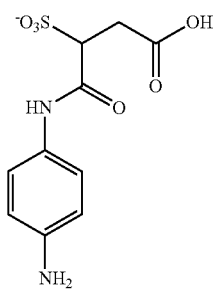

prec-Ia

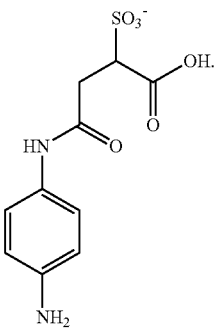

prec-Ib

8. An antiproliferative and/or antibacterial implantable medical device comprising the implantable material according to claim 1.

9. A kit comprising the implantable material according to claim 1 and an inserting and/or implantation device.

10. A compound of Formula (I)

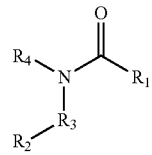

(I)

wherein $R_1$ represents a group substituted by one carboxylate function and one sulfonate function, said group being selected from linear or branched alkyl, aryl, or heteroaryl; said groups being optionally substituted by one or more substituent selected from alkyl, aryl, halogen or carbonyl;

$R_2$ represents an aryl or heteroaryl group substituted by at least one diazonium salt group or at least one primary amine group and optionally further substituted by one or more substituent selected from alkyl, aryl or halogen;

$R_3$ is a bond or represents a linear or branched C1-C3 alkyl group, optionally substituted by one or more substituent selected from alkyl, aryl, heteroaryl, halogen or nitro;

$R_4$ represents a hydrogen atom or a group selected from alkyl, aryl, heteroaryl or alkylcarbonyl.

* * * * *